United States Patent [19]

Patel et al.

[11] Patent Number: 5,141,862
[45] Date of Patent: Aug. 25, 1992

[54] METHOD OF PURIFYING TPA OR PLASMINOGEN ACTIVATOR USING A TRIPEPTIDE OF THE FORMULA: -X-Y-ARGININAL WHEREIN X AND Y ARE SELECTED FROM THE GROUP CONSISTING OF PRO,PHE,TRP AND TYR

[75] Inventors: Arun Patel, King of Prussia; A. Hirotoshi Nishikawa, Haverford, both of Pa.

[73] Assignee: SmithKline Beecham Corporation, Philadelphia, Pa.

[21] Appl. No.: 510,333

[22] Filed: Apr. 17, 1990

[51] Int. Cl.$^5$ .......................... C12N 9/64; C12N 9/48; C12N 9/72

[52] U.S. Cl. .................... 435/226; 435/212; 435/215

[58] Field of Search ................. 435/226, 212, 215

[56] References Cited

U.S. PATENT DOCUMENTS

| | | | |
|---|---|---|---|
| 4.525.465 | 6/1985 | Someno et al. | 502/7 |
| 4.708.944 | 11/1987 | Someno | 435/215 |
| 4.752.581 | 6/1988 | Robinson et al. | 435/217 |
| 4.752.603 | 6/1988 | Collen et al. | 435/226 |
| 4.766.075 | 8/1988 | Goeddel et al. | 435/212 |
| 4.798.796 | 1/1989 | Wilson | 435/226 |
| 4.833.085 | 5/1989 | Schaumann et al. | 435/226 |
| 4.853.330 | 8/1989 | Goeddel et al. | 435/212 |
| 4.892.826 | 1/1990 | Homandberg et al. | 435/212 |

FOREIGN PATENT DOCUMENTS

A39515/89  2/1990  Australia .

OTHER PUBLICATIONS

Patel et al., Biochem Biophys Res Comm., 104:181–186 (1982).
Patel et al., Biochem Biophys Acta, 748:321–330 (1983).

Primary Examiner—David M. Naff
Assistant Examiner—Mike Meller
Attorney, Agent, or Firm—Jeffrey A. Sutton; Stephen Venetianer; Edward T. Lentz

[57] ABSTRACT

A method for purifying tPA or a plasminogen activator having an active site resembling that of tPA from an impure solution thereof which comprises contacting the impure solution with a solid support having bound thereto a tripeptide of the formula: -X-Y-argininal, wherein X and Y are amino acids selected from the group consisting of pro, phe, trp and tyr. The method is also used with a tripeptide of the formula: -phe-Y-argininal, wherein Y is selected from the group consisting of phe, pro, trp, tyr, val, ile and glu(PEA).

13 Claims, No Drawings

METHOD OF PURIFYING TPA OR PLASMINOGEN ACTIVATOR USING A TRIPEPTIDE OF THE FORMULA: -X-Y-ARGININAL WHEREIN X AND Y ARE SELECTED FROM THE GROUP CONSISTING OF PRO,PHE,TRP AND TYR

FIELD OF THE INVENTION

This invention relates to a process for isolating plasminogen activators via an affinity ligand.

BACKGROUND OF THE INVENTION

Fibrinolytic enzymes may be divided into two general classes. The first class of enzymes can be characterized by the ability to directly digest fibrin, and includes trypsin and plasmin. The second class indirectly digests fibrin by activating plasminogen. The latter class, comprising the plasminogen activators (i.e. urokinase and tissue plasminogen activator (tPA)), can be further characterized based on immunological criteria, molecular weight and polypeptide composition (see Collen et al., *Thromb Haemostas,* 48:294-296 (1982)).

In general, the plasminogen activators tend to have a higher substrate specificity than trypsin or plasmin. For example, while both tPA and trypsin recognize an arginine or lysine at the scissile bond site of a substrate, e.g., -X-Y-Arg- ↓ Z-Z'-, trypsin is capable of hydrolyzing a much broader range of peptide sequences. In fact, trypsin is capable of autolysis. tPA by contrast appears to hydrolyze a specific peptide loop in plasminogen and does not autolyze, owing to its high specificity.

The purification of plasminogen activators, most notable tPA, has been the focus of extensive research in recent years. Various protocols have been described for the purification of tPA including: salt precipitation, e.g. ammonium sulfate precipitation (see Rijken et al., *Biochem Biophys Acta,* 580:140 (1979), Meyhack et al., EP-A-143,081); ion exchange chromatography, e.g., zinc chelate agarose (see, Rijken et al., supra, Collen et al., U.S. Pat. No. 4,752,603, Dodd et al., *FEBS,* 209(1):13 (1986)), SP-Sephadex ® (see, Kruithof et al., *J. Biochem.* 226:631-636 (1985)), and CM-Sepharose ® (see, Murakami et al., U.S. Pat. No. 4,552,760). Another commonly used technique in conjunction with the method(s) disclosed above is size exclusion chromatography as taught by Collen et al., U.S. Pat. No. 4,752,603, Murakami et al., U.S. Pat. No. 4,552,760, and Rijken et al., *Biochem Biophys Acta,* 580:140 (1979).

In addition, various affinity chromatography ligands have been used in the purification of tPA. For example, Wallen et al. (*Eur J Biochem,* 133:681-686 (1983)) disclose the use of an anti-porcine tPA affinity ligand. Meyhack et al. (EP-A-143,081) disclose anti tPA antibodies and the *Erythrina latissima* trypsin inhibitor (referred to as ETI or DE-3). Dodd et al. (*FEBS,* 209(1):13 (1986)) report purification of tPA using lysine as an affinity ligand. Murakami et al. (U.S. Pat. No. 4,552,760) suggest using a fibrin Sepharose ® column for tPA purification. Wilson et al., (EP-A-113,319) report several purification schemes, including aminobenzamidine Sepharose ® and DE-3 Sepharose ®; and Wei et al. (EP-A-178,105) disclose the use of a dye (i.e. Trisacryl blue) as an affinity ligand.

Most of these methods are not appropriate for the large scale production of tPA, as they are inefficient in product recovery or are only partially effective in removing impurities. Large scale purification methods which employ immunoaffinity chromatography (e.g., Wallen et al. (*Eur J Biochem,* 133:681-686 (1983)) and Meyhack et al. (EP-A-143,081)) are limited by the cost of the antibody resin, the difficulty in sterilizing this resin and by the potential for the antibodies, or fragments thereof, to leach into the recovered tPA.

Hence the need for a cost-effective affinity ligand to purify plasminogen activators remains. In order to obtain a high degree of purity, a ligand with a high avidity towards a plasminogen activator is needed. The problem then, is to identify such ligands with a high avidity for plasminogen activators, yet without such high avidity that the plasminogen activator cannot be desorbed without denaturation.

SUMMARY OF THE INVENTION

The present invention relates to a method for purifying plasminogen activators having the active site of tPA from an impure solution. This method comprises contacting the impure solution with a solid support having bound thereto a tripeptide of the formula -X-Y-Argininal, where X and Y are hydrophobic amino acids and Argininal is the aldehyde analog of arginine.

This invention also relates to a solid support, having bound thereto the tripeptide of the present invention, -X-Y-Argininal, where X and Y are hydrophobic amino acids and Argininal is the aldehyde analog of arginine.

In related aspects, this invention also comprises a plasminogen activator bound to the tripeptide of the present invention.

DETAILED DESCRIPTION OF THE INVENTION

The present invention relates to a solid support for purifying plasminogen activating enzymes and a method for isolating said plasminogen activating enzymes. The solid support of the invention comprises a tripeptide ligand with a high avidity for plasminogen activating enzymes having the active site of tPA, herein referred to as plasminogen activators, or PA. The ligand - PA avidity must be sufficiently strong so as to adsorb a PA, but must also permit the subsequent desorption or elution without denaturation of the plasminogen activator. In addition, this avidity must be sufficiently selective so as to not adsorb significant amounts of impurities.

The tripeptide ligands of the present invention are active-site directed transition state analogs. These ligands are tripeptide aldehydes of the general formula: -X-Y-Argininal, wherein X and Y comprise hydrophobic amino acids having non polar or polar uncharged substituents. The carboxy terminal peptide is an aldehyde analog of arginine, herein referred to as argininal or Argal.

It is preferable that the amino acid residue in the Y position be hydrophobic in nature. However, it is essential that the amino acid residue in the X position be hydrophobic. Such hydrophobic amino acids include, for example, ala, val, leu, ile, pro, phe, trp, met and tyr. Preferable hydrophobic amino acids include pro, phe, trp and tyr. Other amino acids hydrophobic in nature may include derivatives of non hydrophobic amino acids, for example, glu(PEA) [phenethyl amido]. One of skill in the art will appreciate that use of other amino acid derivatives, hydrophobic in nature, is also encompassed by the present invention. In addition, the present invention is not limited to amino acid residues that form a peptide bond (i.e., —CONH—) between the X and Y positions of the tripeptide ligand. For example, the X and Y residues may form an isosteric linkage. Examples of peptide isosteres are —CH=CH—, —CH$_2$CH$_2$—, —COCH$_2$—, —COO—, —CHOHCH$_2$—, —CH$_2$S— and —NHCO—.

The present invention is not intended to be bound by a particular mechanism of action. However, it is hypothesized that upon association with active site of a PA, the aldehyde moiety of the tripeptide covalently reacts with the catalytic serine alcohol group to form a hemiacetal. This hemiacetal mimics the transition state of the normal PA substrate cleavage reaction (amidolysis) resulting in a covalently bound complex. Hence, variations in the tripeptide ligand may affect the selectivity and/or avidity of the ligand - PA interaction. For example, replacing the carboxy terminal peptide with the alcohol analog of arginine (i.e., Argol) results in a less tightly formed ligand - PA complex without appreciable change in tripeptide selectivity. On the other hand, variations in the X and Y positions of the tripeptide ligand can affect selectivity towards a particular PA.

For example, the tripeptide sequence Pro$^{558}$- Gly$^{559}$- Arg$^{560}$ is found adjacent to the scissile bond or cleavage site of plasminogen, a substrate of both tPA and urokinase (UK). Table III discloses that both tPA and UK bind to the active-site transition state ligand, Pro-Gly-Argal. However, both are readily eluted by a low salt wash indicating a low avidity to this tripeptide ligand. In contrast, the active-site transition-state ligand for a different tripeptide not found adjacent to the scissile bond, Phe-Pro-Argal (Table IV), shows a much higher ligand - PA avidity. Hence there is little, if any, predictive value of naturally occurring substrate sequences as a basis for selecting a particular tripeptide ligand.

The tripeptide aldehyde ligand can be attached to the solid support by a stepwise manner coupling of amino acid residues. Alternatively, one skilled in the art could presynthesize the complete tripeptide aldehyde and attach it in one step to the solid support. The tripeptide aldehyde synthesis on the solid support is from the N-terminus to C-terminus, which is opposite in direction to the commonly used Merrifield solid-phase peptide synthesis. The methods of peptide synthesis, however, are well known in the art, see for example, Ali et al., *J Med Chem*, 29:984 (1986) and *J Med Chem*, 30:2291 (1987).

To introduce argininal at the C terminus, the precursor arginine semicarbazone can first be generated by the method of Patel et al., *Biochem Biophys Res Comm*, 104:181-186 (1982), which is incorporated by reference herein.

Tripeptides as described herein, are useful in affinity purification of PAs from impure solutions. The impure solution can be, e.g., a clarified fermentation broth or conditioned media or any partially purified solution (i.e., 0.1%-95% PA). Unlike chemically unreactive affinity ligands, one which contains an argininal moiety has the potential to non-selectively react with primary and secondary amines in buffers or culture media (e.g., amino acids, peptides, etc.). Therefore, the impure solution containing the plasminogen activator to be purified is preferably at a pH of 8.5 or less. More preferably, the solution containing the plasminogen activator to be purified is at pH 6.0 or lower.

The solid support or solid carrier to which the ligand is coupled can be any material which is insoluble in the buffers or impure solutions employed and which is capable of chemically coupling the ligand. Many such carriers are known. These include glass, silica, alumina, and zirconia as well as organic carriers such as agarose, cellulose, dextran, polyamide, polyacrylamide and vinyl copolymers of bifunctional acrylates with various hydroxylated monomers. Commercially available carriers include, for example, Affi-Gel ®, Sephadex ®, Sepharose ®, Trisacryl ®, Sepharose ®, and Biogel ®.

An advantage of the high avidity ligands described herein is a simplified purification scheme. This method is also expected to facilitate lower costs of purification than currently available methods, e.g. monoclonal antibodies (mAb), fibrin column chromatography, benzamidine agarose followed by several other chromatographic procedures.

Another advantage of the present purification process is that when used in conjunction with a metal chelate affinity capture step and size exclusion chromatography, a protein with purity greater than 95% can be obtained which is designed to meet certain regulatory requirements for a pharmaceutical product (e.g., clearance of DNA, viral kill steps, etc.).

Yet another advantage of the present invention includes a greater latitude for adsorbing the plasminogen activator. For example, a pH range of 3.0 to 8.5, preferably 3.5 to 6.0 can be used. Furthermore, no specific desalting step is required after the desorbing operation. tPA for example, can be eluted and recovered in a high yield from the adsorbent by merely lowering the pH. This invention, however, is not limited to the purification of tPA, but includes other plasminogen activators which possess the same, or substantially the same, active site as tPA. As used herein, the term "active site of tPA" refers to plasminogen activators capable of adsorbing to transition state tripeptides, as described herein, which remain bound during high ionic strength wash conditions (e.g., 1.0M salt at neutral pH), yet can be desorbed by a change in pH (e.g., elution by 0.1M acetic acid). In addition the "active site of tPA" refers to serine protease activity, which can be determined chromogenically, e.g., the S-2251 assay (Weinberg et al., *J Immunol Meth*, 75:289 (1984)) or by alternate methods, for example, clot lysis activity as described by Granelli-Piperno et al. (*J Exp Med*, 148:223 (1978)). Thus plasminogen activators having the same, or substantially the same, active site of tPA have a high avidity for transition state tripeptides of the present invention and also possess serine protease activity, as defined above, which is substantially the same, if not greater, than the serine protease activity of wild type tPA.

Plasminogen activators include, for example, tPA and variants thereof, which possess the same or substantially the same active site of tPA such as variants in which one or more amino acids have been added, deleted, rearranged, or substituted. Such variants also encompass molecules in which one or more functional domains have been added, deleted or altered such as by combining the active site of one plasminogen activator, e.g., tPA, with the fibrin binding domain of another plasminogen activator, e.g., one or more kringle regions from urokinase or plasminogen, or with another fibrin binding molecule such as a Fab fragment of an anti-fibrin IgG molecule (see for example, Runge et al., *Proc Natl Acad Sci*, 84: 7659 7662 (1987).

Other variants include tPA molecules in which the primary amino acid sequence has been altered in the growth factor domain so as to increase the serum halflife of the plasminogen activator. Such tPA growth factor variants are disclosed for example, by Browne, EP-A-0,240,334 (Published Oct. 7, 1987), Kalyan et al., W088/05822 (Published, Aug. 11, 1988), and Cassani et al., EP-A-0,308,716 (Published, Mar. 29, 1989; urokinase variants).

Preferred plasminogen activator variants include the substitution mutations BBNT5 and BBNT12, both disclosed in G.B. patent application serial number GB 8815135.2, filed Jun. 24, 1988. BBNT5 consists of two substitution mutations in wild type tPA, $Tyr^{67}$ to Ser and $Phe^{68}$ to Ser. BBNT12 embodies 3 substitutions, $Leu^{66}$ to Asp, $Tyr^{67}$ to Asp, and $Phe^{68}$ to Thr.

Further examples of preferred plasminogen activators, purified by the present invention, are hybrids comprising the active site of tPA, e.g. the B chain of tPA, with other sequences, e.g., the A-chain of plasmin, see Robinson et al., U.S. Pat. No. 4,752,581. Another preferred variant is disclosed by Browne et al., EP-A-297,882 (Published Jan. 4, 1989). This molecule, referred to as H37, is a plasminogen (amino acids 1-541) - tPA (amino acids 262-527) hybrid and referred to herein as mut 222. Other variants include fusions of the active site of tPA to other plasminogen activators, e.g. urokinase, pro-urokinase, streptokinase.

Yet further examples of plasminogen activators having the active site of tPA are glycosylation mutants of tPA such as disclosed, for example, by Wei et al., EP-A-0,178,105 (Published. Apr. 16, 1986), Haigwood et al., EP-A-0,227,462 (Published, Jul. 1, 1987), Meyhack et al., EP-A-0,225,286 (Published. Jun. 10, 1987), and Baltimore et al., EP-A-0,299,706 (Published, Jan. 18, 1989).

Although it is not required, it is preferable to employ an initial capture step which results in isolation of most of the plasminogen activator while substantially reducing the volume of the impure solution for further purification. This initial capture step relies on a solid support capable of handling a large volume of impure solution (e.g. culture media or any other solution that contains a PA either impure or in a partially purified state, e.g. 0.1-95% PA), at a high flow rate and with a high efficiency. Examples of such chromatography include, for example, immobilized ligands such as metal chelating agents, lysine, arginine, fibrin, ETI, various dyes (e.g. Trisacryl Blue), boronic acid, phenylboronate, concanavalin A, p-aminobenzamidine and benzamidine. The preferred capture step is metal chelate chromatography, especially zinc chelate chromatography. Such a technique is generally described by Porath et al., *Nature*, 258:598 (1975). The support can be, e.g., a soft gel such as dextran, agarose or polyacrylamide gel, a rigid gel such as Fractogel ® vinyl polymer gel, 32-63 mm size (Pierce Chemical Co., Rockford, Ill.) or any other support capable of adsorbing PA.

As disclosed by DePhillips et al., U.S. patent application Ser. No. 07/056,927, filed Jun. 3, 1987, and incorporated by reference herewith, the purification by the zinc chelate column can be enhanced by the washing of the adsorption support by water below pH 5.0 in an aqueous solution of an alkali or alkaline earth metal salt e.g., NaCl, KCl, $MgCl_2$, $CaCl_2$ or a chaotrope, e.g., guanidine, thiocyanate, or urea.

It has been found, for example, that washing a zinc chelate column at about neutral pH in accordance with the standard procedure does not remove a significant amount of contaminants from the conditioned medium. A second wash at pH less than 5.0 unexpectedly removes a significant amount of further contaminants. For example, in a representative experiment in which a zinc chelate column was washed completely with water buffered to pH 6.0 and then with water buffered to pH 4.5, the first wash removed contaminants approximately equal to the amount of tPA and the second wash removed an unexpectedly large amount of contaminants equal to about 10% of the amount of tPA as determined by comparison of peaks in a chromatogram showing absorbance at 280 nm.

The impure solution obtained from the capture step is now partially purified such that the tPA (or other plasminogen activators) is at least 50% pure and preferably 75 to 95% pure, based on total protein content by reverse phase chromatography, SDS-PAGE, or any other standard means to quantitate proteins.

Prior to absorption to the tripeptide ligand, the eluant from above containing the plasminogen activator may be further concentrated by selective precipitation, for example, ammonium sulfate ppt., immunoprecipitation, and isoelectric precipitation. The impure solution is next adsorbed onto a tripeptide affinity support. Both the D- and the L-enantiomers were equally effective as tripeptide ligands, however the D-enantiomers are preferable due to a greater resistance to proteolytic cleavage.

The affinity support is washed at neutral pH with a low salt, and subsequently a high salt (e.g., 1.0M) wash. The salt is then removed by additional low salt washes prior to elution. The selectively bound plasminogen activator may then be desorbed with an eluant of pH less than 6.0 or greater than 8.0 and may or may not contain a strong nucleophile like hydroxylamine or semicarbazide. Preferably the plasminogen activator is eluted with 0.1-1.0M acetic acid; more preferably with 0.2-0.4M acetic acid.

Following the tripeptide column adsorption/elution, one more step may be desirable to produce a plasminogen activator product of pharmaceutical grade. This can be, for example, ion exchange chromatography or size exclusion chromatography. Preferably, it is size exclusion chromatography.

The size exclusion step is carried out using a small particle packing, e.g., less than about 50 $\mu$m, having a separation range of 1000 to 300,000 molecular weight. By the use of such gel, residual traces of high molecular weight contaminants can be removed. For example, Superose ® 12 cross linked agarose (Pharmacia, Piscataway, N.J.), which has an average particle size of 20-40 $\mu$m and a separation range of 1,000 to 300,000 molecular weight, has been discovered to readily separate tPA, (molecular weight of about 70,000 Daltons), from high molecular weight (greater than 90,000 Daltons) contaminants. Such separation of physically similar proteins by size exclusion chromatography removes residual PA aggregates, including dimers, nucleic acids and, if present, virus particles.

Fractions from the size exclusion step which contain the plasminogen activator are collected for final formulation, sterile filtration and packaging. Prior to final formulation, salt can be removed by, e.g. dialysis, diafiltration, or a desalting column, for example, Sephadex ® G-25, Biogel ® P2 or Biogel ® P4.

The examples which follow are illustrative, but not limiting of the present invention.

EXAMPLES

Amino acids and protected derivatives were purchased from Bachem Bioscience Inc. (Philadelphia, Pa.). Affi-Gel-10 was obtained from Bio-Rad Labs (Richmond, Calif.). Chromogenic enzyme substrates were purchased from Helena Labs (Texas). Bovine thrombin was from Miles Diagnostics (Kankakee, Ill.). Urokinase was obtained from Calbiochem (San Diego, Calif.). tPA was obtained from in-house sources, it is also available commercially (e.g. American Diagnostic, New York, N.Y.). Other specialty chemicals were procured from Sigma Chemical Co. (St. Louis, Mo.). Arginine semicarbazone was synthesized according to Patel et al., *Biochem Biophys Res Comm*, 104:181–186 (1982).

Example 1. Synthesis of E-SEP-EDA-SA 1.0 liter of Sepharose Cl-6B (Pharmacia Fine Chemicals, catalog #17 0480 01) was reacted with 52.5 ml epibromohydrin in a basic solution of 0.5N NaOH/30% tetrahydrofuran (THF) at 40° C. for four hours. The activated sepharose was collected by filtration on a sintered glass funnel and was washed extensively with 30% THF to remove unreacted epibromohydrin. The product was further washed with water until the washing was neutral. This gel was then resuspended in 1.0 liter of water and was allowed to react with ethylenediamine (50 ml) overnight at room temperature. The gel was filtered and unreacted ethylenediamine was removed by washing the gel with 0.1M acetic acid followed by water. The gel was resuspended in 1.0 liter of water, then was reacted with succinic anhydride (25 gm) at pH 6.0. The gel was further washed with 1.0 liter of a sodium carbonate solution (0.2M) followed by water until the washing was found to be neutral. This gel was finally washed with isopropyl alcohol and stored at 4° C. for further use as a moist powder. This gel is herein referred to as E-SEP-EDA-SA.

Example 2. Synthesis of E-SEP-EDA-SA-X-Y-Argal

The "X", "Y" and ArgSC (semicarbazide protecting group) groups were coupled sequentially to the succinyl moiety using a water-soluble carbodiimide [N ethyl N'-(3-dimethyl-aminopropyl)-carbodiimide hydrochloride] (or EDAC), triethylamine (TEA), isopropyl alcohol (IPA), and N hydroxybenzotriazole (HOBT). The X and Y groups were added as methyl ester derivatives and followed by saponification with 0.1M sodium carbonate as described by Bogdanszky (*Principles of Peptide Synthesis*, Chap. 3, Springer-Verlag, Berlin (1984)). The ArgSC was added as described by Patel et al., supra. The semicarbazide protecting group was removed by treatment with formaldehyde in dilute acetic acid. The schematic of this synthesis is shown in Table I.

TABLE I

Synthesis of E—SEP—EDA—SA—X—Y—Argal

E—SEP—EDA—SA

↓ IPA wash

Room temp. 6 hours | IPA, HOBT, Amino acid-OCH₃ (X position), EDAC, TEA

↓

Room temp. Overnight | 0.1M Na₂CO₃

↓

H₂O wash
IPA wash

Room temp. 6 hours | IPA, HOBT, Amino acid-OCH₃ (Y position), EDAC, TEA

↓ IPA wash

Overnight | 0.1M Na₂CO₃

↓

H₂O wash
IPA wash

Room temp. 6 hours | ArgSC, EDAC, HOBT, TEA

↓ IPA wash

| HCHO, CH₃COOH, H₂O:CH₃OH (50:50)

↓

0.2M Na₂CO₃ wash
H₂O wash

Example 3. Binding of Plasminogen Activators to Affinity Adsorbents

Affinity supports containing a variety of tripeptide sequences were synthesized as described above and were tested for PA binding. In a typical binding experiment, 1 to 40 μg of plasminogen activator (PA) in 10 ml of 0.1M NaOAc containing 0 to 1M NaCl at pH 4.5 was passed through an affinity column (5ml) at a rate of 1 ml/min. The column was then washed with 0.1M sodium phosphate buffer at pH 7.0 followed by additional washes of the same buffer with increased ionic strength by addition of salt to a final concentration of 1.0M. The selectively bound enzyme was eluted with 0.1M acetic acid at 0.3 ml/min.

Samples were assayed with appropriate chromogenic substrates at room temperature. Absorbance changes were recorded in a spectrophotometer for 300 secs. tPA samples (50 μl) were added to a solution containing 0.1M Tris/0.01% PEG-3400, pH 8.1 (900 μl) and 50 μl 0.01M D-Ile-Pro-Arg-pNA.HCl (or S-2288); also assayed was substrate S-2251 (Kabi Group, Greenwich, Conn.) by the method of Conners et al. (DNA, 7:651 661 (1988)). Where appropriate, samples were diluted so that linear absorbance tracings were obtained during the enzyme reactions.

The tPA concentration was determined using various standard assays including HPLC, the S2251 Assay, the particle fluorescence immunoassay (PCFIA) performed according to the protocol provided by the manufacturer (Pandex Laboratories Inc., Mundelein, Ill.), and the enzyme immunoassay (EIA) performed substantially as described in the protocol provided by the manufacturer (American Diagnostica, New York, N.Y.).

For trypsin activity determination, trypsin samples (100 μl) were added to 900 μl of Tris buffer (see tPA) and 100 μl of 0.01M tosylarginine methyl ester in water; absorbance was measured at 247 nm. Urokinase samples (200 μl) were added to 800 μl of Tris buffer (see tPA) and 50 μl of 0.003M pyr-Glu-Gly-Arg-pNA.HCl (S-2444); absorbance was measured at 405 nm. Thrombin samples (50 μl) were added to 900 ml of Tris buffer (0.1M Tris/0.25M CaCl$_2$/0.01% PEG-3400 pH 8.1) and 50 μl of 0.002M D-Phe-Pip-Arg-pNA (S-2238); absorbance was measured at 405 nm.

Table II discloses a tripeptide ligand with a greater selective affinity for trypsin than myeloma-derived tPA. Trypsin and tPA are known to recognize the tripeptide sequence Arg-Leu-Arg of ETI (erythrina trypsin inhibitor). Hence the transition state analog, Arg-Leu-Argal, was synthesized for binding studies. As shown in Table II, tPA initially absorbed to this ligand, but was readily desorbed. In contrast, trypsin absorbed this ligand with a much higher avidity, such that only 10% of the affinity bound enzyme could be released.

TABLE II

| Binding to Affi-10-Arg—Leu—Argal | | |
|---|---|---|
| | % Activity | |
| | Trypsin | tPA |
| load | 100% | 100% |
| flow through | 2 | 0 |
| 0.2M NaCl/buffer wash | 2 | 49 |
| 1.0M NaCl/buffer wash | 2 | 53 |
| 0.2N NH$_4$OH elution | 10 | 8 |

In naturally occurring plasminogen, the tripeptide sequence Pro-Gly-Arg is found adjacent to the scissile bond. In searching for a more avid tripeptide, the transition state ligand Pro-Gly-Argal was synthesized. Table III shows that both tPA and urokinase (UK) initially bound to the affinity ligand. tPA was readily desorbed with buffer, while a smaller but significant amount of UK required low pH to allow release of the enzyme.

TABLE III

| Binding to EDA*—SA—Pro—Gly—Argal | | |
|---|---|---|
| | % Activity | |
| | tPA | UK |
| load | 100% | 100% |
| flow through | 1 | 0 |
| 0.1M buffer wash | 81 | 48 |
| 1M NaCl/ buffer | 7 | 9 |
| 0.1M Acetic acid | 6 | 21 |

EDA* = E—SEP—EDA

Table IV shows that the tripeptide Phe-Pro-Argal is fairly effective in capturing and purifying tPA. Quite unexpected, however, was a difference in ligand affinity depending upon the chain content of the tPA. Preparations where the cell line and/or culture conditions yielded primarily single-chain tPA (e.g., myeloma-derived) shared a weaker ligand binding than predominantly two-chain tPA (e.g., CHO-derived).

TABLE IV

| Binding to EDA*—SA—D—Phe—Pro—Argal | | |
|---|---|---|
| | % Activity | |
| | tPA* | tPA** |
| load | 100% | 100% |
| flow thru | 1 | 0 |
| low salt | 33 | 4 |

TABLE IV-continued

| Binding to EDA*—SA—D—Phe—Pro—Argal | | |
|---|---|---|
| | % Activity | |
| | tPA* | tPA** |
| high salt | 2 | 1 |
| 0.1M HOAc | 74 | 84 |

Assay with S-2288
*One Chain
**Two chain.

Various tripeptide ligands were synthesized with hydrophobic residues in the X and Y positions. Table V shows those ligands which were screened and found not effective in tPA binding.

TABLE V

| Binding of Myeloma tPA to Affinity Adsorbents | | | |
|---|---|---|---|
| | % Enzyme Ativity | | |
| Ligand | Unbnd | Wash | Recvd* |
| D—Phe—L—Ala—Argal | 0 | 24 | 54 |
| L—Ile—L—Ala—Argal | 0 | 73 | 3 |
| L—Ile—D—Phe—Argal | 0 | 98 | 8 |
| L—Val—D—Phe—Argal | 0 | 92 | 10 |
| L—Ala—D—Phe—Argal | 0 | 64 | 34 |
| L—Tyr—L—Ala—Argal | 1 | 55 | 31 |
| L—Tyr—L—Val—Argal | 0 | 87 | 25 |
| L—Gln—L—Gly—Argal | 0 | 98 | 5 |
| L—Pro—L—Gly—Argal | 1 | 88 | 7 |
| L—Glu(PEA)—D—Phe—Argal | 0 | 42 | 34 |

*0.1M HOAc

Table VI lists tripeptide ligands with hydrophobic residues in the X and Y positions which were found to be effective in binding tPA.

TABLE VI

| Binding of Myeloma tPA to Affinity Adsorbents | | | |
|---|---|---|---|
| | % Enzyme Activity | | |
| Ligand | Unbnd | Wash | Recvd* |
| D—Phe—D—Phe—Argal | 1 | 0 | 72 |
| L—Phe—D—Phe—Argal | 1 | 0 | 58 |
| L—Phe—L—Phe—Argal | 0 | 0 | 74 |
| D—Phe—L—Phe—Argal | 0 | 0 | 53 |
| D—Phe—L—Trp—Argal | 1 | 0 | 64 |
| D—Phe—L—Val—Argal | 0 | 3 | 80 |
| D—Phe—L—Ile—Argal | 0 | 0 | 59 |
| D—Phe—L—Tyr—Argal | 0 | 0 | 63 |
| L—Tyr—D—Phe—Argal | 0 | 1 | 78 |
| L—Trp—D—Phe—Argal | 0 | 0 | 50 |
| D—Phe—L—Glu(PEA)—Argal | 0 | 0 | 72 |

*0.1M HOAc

As noted in Table IV, there is a differential affinity between the one-chain and two-chain forms of tPA for ligand D-Phe-D-Pro-Argal. However, since both forms of tPA act similarly in vivo, it is of interest to isolate both equally as well in any purification scheme. Table VII show a different affinity ligand for the two forms of tPA. Despite a difference in affinity, the bulk of the tPA was recovered in the acetic acid eluant.

TABLE VII

| Binding of tPA to EDA*—SA—D—Phe—D—Phe—Argal | | |
|---|---|---|
| | % Activity | |
| | tPA (CHO)* | tPA (myeloma)** |
| unbound | 7% | 1% |
| 1st phosphate wash | <1 | 0 |
| 2nd phosphate wash | 0 | 0 |
| 1st phosphate/1M NaCl wash | <1 | 0 |
| 2nd phosphate/1M NaCl wash | 0 | 0 |
| 1st 0.1M HOAC elution | 0 | 0 |
| 2nd 0.1M HOAC elution | 0 | 68 |

TABLE VII-continued

| Binding of tPA to EDA*—SA—D—Phe—D—Phe—Argal | | |
|---|---|---|
| | % Activity | |
| | tPA (CHO)* | tPA (myeloma)** |
| 3rd 0.1M HOAC elution | 70 | 3 |
| 4th 0.1M HOAC elution | 12 | — |

*Predominantly two chain.
**Predominantly one chain.

Further studies of the ligand D-Phe-d-Phe-Argal demonstrated a very selective protease affinity. See Table VIII.

TABLE VIII

| Binding of Proteases to EDA*—SA—D—Phe—D—Phe—Argal | | | |
|---|---|---|---|
| | % Activity | | |
| | tPA (Myeloma) | Thrombin | Urokinase |
| unbound | 1% | 6% | 1% |
| low salt wash | 0 | 20 | 3 |
| high salt wash | 0 | 0 | 11 |
| 0.1M HOAC | 71 | 4 | 43 |

Finally, in contrast to the other examples, Table IX shows a dipeptide affinity ligand. The results summarized below imply that the Argal residue has a significant effect on enzyme binding.

TABLE IX

| Proteases Binding to EDA*—SA—D—Phe—D—Phe | | | | | |
|---|---|---|---|---|---|
| | tPA[1] | tPA[2] | UK[3] | Thrmb[4] | Trp[5] |
| unbound | 0% | 22% | <1% | 0% | 2% |
| low salt wash | 1 | 18 | 36 | 0 | 72 |
| high salt wash | 7 | 11 | 22 | 1 | 11 |
| 0.1M HOAC | <1 | 5 | 9 | 3 | 8 |

[1] from CHO cells; 2-chain;
[2] from myeloma cells; 1-chain;
[3] urokinase;
[4] thrombin;
[5] trypsin Example 4. Purification of tPA Recombinant tPA was expressed in a myeloma cell line in a conditioned medium composed of 2% Bovine serum albumin (BSA), transferrin, basal media e.g., MEM, and Excyte at 2 mg/L (a complex lipid supplement isolated from bovine serum). Four liters of a packed cell matrix was perfused at a rate of approximately 25 liters per day.

Chelating Sepharose® Fast Flow from Pharmacia (Piscataway, N.J.) was used for the Metal Chelate Affinity resin, see Porath et al., Nature, 258:598-599 (1975). A 3 to 6 Liter column was used in a column with a 500 cm² cross sectional area. The media loading and all the wash steps were performed at 4° C. at a flow rate of 240 cm/hr. Elution was at a slower flow rate, i.e. 120 cm/hr to keep the eluate volumes small. ZnCl₂ was used to charge the resin and was added to the media at 10 ppm prior to loading. Following loading the column was washed with 5 column volumes of 0.1M NH₄Ac, pH 6.0 and then with 2-3 column volumes of 0.1M NH₄Ac/0.1M NaCl, pH 4.5. Elution was effected by 0.1M NH Ac/0.5M NaCl, pH 4.5. The column capacity for the crude tPA was approximately 2 grams per liter of resin.

The vast majority of media components pass through the column without being retained, while the tPA is quantitatively retained. The wash at pH 6.0 removes a large percentage of the residual BSA. The pH is then lowered to 4.5 in the presence of 100 mM NaCl to remove a heterogeneous population of proteins. tPA will begin to elute if more than three column volumes of this buffer are applied to the column. The tPA is then eluted at 500 mM NaCl, pH 4.5. These elution conditions are distinctly different from those originally worked out for tPA (Rijken et al., J Biol Chem, 256:1035-1041 (1981)), which operated at pH 7.0 and affected elution with a histidine gradient. Fractions containing tPA as determined by the S-2251 assay (Weinberg et al., J Immunol Meth, 75:289 (1984)) were pulled for further processing.

tPA was then concentrated by isoelectric precipitation. The zinc chelate eluate was adjusted to pH 7.0 with 1.0N NaOH and the mixture was stirred for 30 min at 4° C. The precipitate was then collected by centrifugation at 5,000×g. The pellet was then resuspended by the addition of 0.1M acetic acid. Following solubilization the material was adjusted to 300 mM NaCl with 600 mM NaCl/0.1M NH₄Ac, pH 4.0.

This protein was then dissolved in 0.1M acetic acid/0.3M NaCl, pH 4.5 and applied to a 420 ml (5×20 cm) tripeptide affinity adsorbent column pre equilibrated with 0.1M sodium acetate buffer, pH 4.5. The resin selected for the purification of myeloma tPA was D-Phe-D-Phe-Argal (see Example 3). The column was then washed with 0.1M sodium phosphate buffer at pH 7.0 followed by additional washes of the same buffer with increased ionic strength by the addition of NaCl to a final concentration of 1.0M. This wash serves to flush out any serum albumin contaminant. This was followed by a dilute pH 7.0 sodium phosphate buffer to wash out the NaCl. The selectively bound enzyme was eluted with 0.1M acetic acid. Yields were typically 95% for this step, and protein purity routinely exceeded 95%.

As a final step, the eluate from the tripeptide affinity adsorbent column was concentrated on a tangential flow apparatus using 10 kD nominal molecular weight cutoff membranes. Sodium chloride was added to bring the salt concentration to 200 mM. The eluate was then applied to a Superose® 12 column equilibrated with 200 mM NaCl and 100 mM HOAc at room temperature. A peak migrating near the void of the column was determined to be tPA by SDS-PAGE under reducing conditions. The tail of the product was not pooled with the rest of the material as it contains low molecular weight contaminants. Each step results in a high percent recovery and the use of only three chromatograph steps results in a total recovery of approximately 76%.

The above description and examples fully disclose the invention including preferred embodiments thereof. However, it is appreciated that the invention is not limited to the particular embodiments described above. Modifications of the methods described above that are obvious to those of ordinary skill in the art are intended to be within the scope of the following claims.

What is claimed is:

1. A method for purifying tPA or a plasminogen activator having an active site resembling that of tPA from an impure solution thereof which comprises contacting the impure solution with a solid support having bound thereto a tripeptide of the formula:

-X-Y-argininal wherein X and Y are amino acids selected from the group consisting of pro, phe, trp and tyr.

2. The method of claim 1 wherein X and Y are selected from the group consisting of pro, phe, and tyr.

3. The method of claim 1 wherein the tripeptide is selected from the group consisting of -phe-pro-argininal, -phe-phe-argininal and -phe-tyr-argininal.

4. The method of claim 1 wherein the tripeptide is -D-phe-D-phe-argininal.

5. The method of claim 1 wherein the tripeptide is covalently bound to the solid support.

6. The method of claim 1 wherein the tripeptide is bound to the solid support by a peptide bond.

7. The method of claim 1 wherein the pH of the impure solution is 3.0 to 8.5.

8. The method of claim 1 which further comprises eluting the plasminogen activator bound to the tripeptide with an eluant of pH less than 6.0.

9. The eluant of claim 10 which has a pH of less than or equal to 4.5.

10. The method of claim 1 which first comprises an initial capture step of the impure solution.

11. The method of claim 10 wherein the initial capture step comprises contacting the impure solution with a metal chelate affinity support, and subsequently eluting the plasminogen activator from said affinity support prior to contact with the tripeptide support.

12. A method for purifying tPA or a plasminogen activator having an active site resembling that of tPA from an impure solution thereof which comprises contacting the impure solution with a solid support having bound thereto a tripeptide of the formula:

-phe-Y-argininal wherein Y is an amino acid selected from the group consisting of phe, pro, trp, tyr, val, ile and glu(PEA).

13. The method of claim 12 wherein Y is selected from the group consisting of val, ile and glu(PEA).

* * * * *

UNITED STATES PATENT AND TRADEMARK OFFICE
CERTIFICATE OF CORRECTION

PATENT NO. : 5,141,862

DATED : Aug. 25, 1992

INVENTOR(S) : Arun Patel, A. Hirotoshi Nishikawa

It is certified that error appears in the above-identified patent and that said Letters Patent is hereby corrected as shown below:

Column 13, Line 19, change "of claim 10" to -- of claim 8 --.

Signed and Sealed this

Twelfth Day of October, 1993

Attest:

BRUCE LEHMAN

Attesting Officer

Commissioner of Patents and Trademarks